United States Patent
Welch et al.

(10) Patent No.: US 9,682,134 B2
(45) Date of Patent: Jun. 20, 2017

(54) MOVABLE WALL PANEL SYSTEM WITH ELECTRICAL CONNECTIONS

(71) Applicant: Modernfold, Inc., Greenfield, IN (US)

(72) Inventors: Bryan Thomas Welch, Noblesville, IN (US); Robert Kevin Schuyler, Lapel, IN (US)

(73) Assignee: Modernfold, Inc., Greenfield, IN (US)

( * ) Notice: Subject to any disclaimer, the term of this patent is extended or adjusted under 35 U.S.C. 154(b) by 0 days.

(21) Appl. No.: 15/248,893

(22) Filed: Aug. 26, 2016

(65) Prior Publication Data

US 2017/0093100 A1    Mar. 30, 2017

Related U.S. Application Data

(63) Continuation of application No. 13/251,547, filed on Oct. 3, 2011, now Pat. No. 9,455,561.

(60) Provisional application No. 61/388,786, filed on Oct. 1, 2010.

(51) Int. Cl.
*E04B 1/346* (2006.01)
*A61K 39/08* (2006.01)
*A61K 38/48* (2006.01)

(52) U.S. Cl.
CPC .......... *A61K 39/08* (2013.01); *A61K 38/4893* (2013.01); *Y10S 514/912* (2013.01)

(58) Field of Classification Search
CPC .. A61K 39/08; A61K 38/4893; Y10S 514/912
USPC ....... 52/71, 243.1; 160/199, 229.1; 439/215, 439/502, 527, 557, 650
See application file for complete search history.

(56) References Cited

U.S. PATENT DOCUMENTS

| | | | | |
|---|---|---|---|---|
| 2,447,026 A | | 8/1948 | O'Brien et al. | |
| 2,947,041 A | * | 8/1960 | Imbrecht | E04B 2/822 29/897.32 |
| 4,043,626 A | * | 8/1977 | Propst | E04B 2/7425 174/101 |
| 4,214,799 A | * | 7/1980 | Biche | H02G 3/288 174/505 |
| 4,270,020 A | * | 5/1981 | Kenworthy | H02G 3/288 174/497 |
| 4,313,646 A | * | 2/1982 | Millhimes | H01R 31/02 439/215 |
| 4,370,008 A | * | 1/1983 | Haworth | E04B 2/7425 439/165 |
| 4,375,010 A | * | 2/1983 | Mollenkopf | H02G 3/288 160/127 |

(Continued)

OTHER PUBLICATIONS

Modernfold, Inc., Acousti-Seal Operable Partitions product brochure, Mar. 2008, 24 pages.

(Continued)

*Primary Examiner* — Basil Katcheves
*Assistant Examiner* — Joshua Ihezie
(74) *Attorney, Agent, or Firm* — Faegre Baker Daniels LLP

(57) ABSTRACT

A movable wall panel system induces a plurality of movable wall panels. A first electrical connector of one panel is automatically coupled to a second electrical connector of an adjacent panel as the panels are moved from a folded storage position to an extended use position to electrically couple the adjacent panels together automatically. At least one of the plurality of panels has an electrical receptacle coupled to its associated first and second electrical connectors to provide an electrical power outlet.

7 Claims, 10 Drawing Sheets

(56) References Cited

U.S. PATENT DOCUMENTS

| | | | | |
|---|---|---|---|---|
| 4,376,561 | A * | 3/1983 | Vanden Hoek | E04B 2/7427 439/210 |
| 4,429,938 | A * | 2/1984 | Flor | H01R 13/625 403/349 |
| 4,837,891 | A | 6/1989 | Toma et al. | |
| 4,862,659 | A * | 9/1989 | Wilson | E04B 2/7422 174/499 |
| 5,042,555 | A | 8/1991 | Owens | |
| 5,044,971 | A * | 9/1991 | Hollingsworth | H02G 3/288 439/215 |
| 5,096,433 | A * | 3/1992 | Boundy | H02G 3/288 439/215 |
| 5,097,643 | A * | 3/1992 | Wittler | E04B 2/7425 160/135 |
| 5,112,240 | A | 5/1992 | Nienhuis et al. | |
| 5,152,332 | A | 10/1992 | Siener | |
| 5,159,793 | A * | 11/1992 | Deugo | E04B 2/7409 52/126.1 |
| D335,624 | S | 5/1993 | Siener | |
| 5,207,037 | A | 5/1993 | Giles et al. | |
| 5,214,889 | A * | 6/1993 | Nienhuis | E04B 2/7425 403/254 |
| 5,244,401 | A | 9/1993 | Russell et al. | |
| 5,329,857 | A | 7/1994 | Owens | |
| 5,339,881 | A | 8/1994 | Owens | |
| 5,358,023 | A | 10/1994 | Owens | |
| 5,467,559 | A | 11/1995 | Owens | |
| 5,499,671 | A * | 3/1996 | Owens | E05D 15/26 16/94 R |
| 5,551,499 | A | 9/1996 | McRoberts | |
| 5,562,469 | A * | 10/1996 | Nienhuis | E04B 2/7425 439/215 |
| 5,595,495 | A | 1/1997 | Johnson et al. | |
| 5,806,258 | A * | 9/1998 | Miedema | E04B 2/7437 52/220.7 |
| 5,905,229 | A * | 5/1999 | McKitrick | H02G 3/288 174/495 |
| 6,098,695 | A * | 8/2000 | Schwingle | E05F 15/605 16/87 R |
| 6,349,517 | B1 * | 2/2002 | Manley | E04B 2/7435 160/135 |
| 6,374,456 | B1 | 4/2002 | Fort et al. | |
| 6,393,772 | B1 | 5/2002 | McRoberts et al. | |
| 6,430,779 | B1 | 8/2002 | Goldsmith et al. | |
| 6,481,359 | B1 | 11/2002 | Owens | |
| 6,497,075 | B1 * | 12/2002 | Schreiner | A47B 21/06 52/127.6 |
| 6,516,575 | B2 * | 2/2003 | Haab | E05D 13/04 160/196.1 |
| 6,571,855 | B1 | 6/2003 | Goldsmith et al. | |
| 6,572,238 | B1 | 6/2003 | Johnson | |
| 6,575,777 | B2 * | 6/2003 | Henriott | H01R 25/162 439/215 |
| 6,581,242 | B2 | 6/2003 | Owens | |
| 6,581,345 | B2 * | 6/2003 | Goldsmith | E04B 2/827 52/238.1 |
| 6,598,355 | B2 * | 7/2003 | Owens | E04B 2/827 16/87 R |
| 6,698,491 | B2 * | 3/2004 | Goldsmith | E05D 15/063 160/185 |
| 6,715,530 | B2 * | 4/2004 | Goldsmith | E05D 15/26 160/199 |
| 6,902,415 | B2 * | 6/2005 | Ramsey | H01R 25/006 174/481 |
| 6,910,903 | B2 * | 6/2005 | Kondas | H01R 25/16 174/68.1 |
| 7,185,589 | B2 | 3/2007 | Owens | |
| 7,621,774 | B2 * | 11/2009 | Hayes | H01R 25/16 174/72 A |
| 7,651,353 | B2 * | 1/2010 | Laukhuf | H01R 13/652 439/211 |
| 7,690,934 | B2 | 4/2010 | Riner | |
| 7,699,089 | B2 * | 4/2010 | Knutson | E05F 15/605 160/196.1 |
| 7,699,631 | B2 | 4/2010 | Knepper | |
| 7,826,202 | B2 * | 11/2010 | Johnson | H01R 25/16 307/11 |
| 7,946,883 | B2 * | 5/2011 | Hayes | H01R 25/16 439/502 |
| 8,172,589 | B2 * | 5/2012 | Johnson | H01R 25/16 174/60 |
| 9,455,561 | B2 * | 9/2016 | Welch | H01R 25/162 |
| 2001/0032424 | A1 * | 10/2001 | Goldsmith | E04B 2/827 52/238.1 |
| 2002/0137381 | A1 * | 9/2002 | Chapman | H01R 13/639 439/215 |
| 2003/0141024 | A1 * | 7/2003 | Goldsmith | E05D 15/063 160/199 |
| 2003/0183350 | A1 * | 10/2003 | Goldsmith | E05D 15/26 160/199 |
| 2005/0124195 | A1 * | 6/2005 | McCoy | H01R 29/00 439/201 |
| 2005/0241781 | A1 * | 11/2005 | Johnson | E05F 15/51 160/199 |
| 2007/0125008 | A1 * | 6/2007 | Gallant | A61G 7/00 52/36.4 |
| 2009/0241438 | A1 * | 10/2009 | Gallant | E04B 2/74 52/36.5 |
| 2010/0190369 | A1 * | 7/2010 | Byrne | H01R 4/185 439/215 |

OTHER PUBLICATIONS

International Search Report and Written Opinion from corresponding PCT Application PCT/2011/054571, 10 pages, Nov. 22, 2012.

* cited by examiner

MOVABLE WALL PANEL SYSTEM WITH ELECTRICAL CONNECTIONS

CROSS REFERENCE TO RELATED APPLICATION

This application is a continuation of U.S. patent application Ser. No. 13/251,547, filed Oct. 3, 2011, which claims the benefit of U.S. Provisional Application Ser. No. 61/388,786, filed on Oct. 1, 2010, both of which are incorporated herein by reference.

BACKGROUND AND SUMMARY

The present disclosure relates to movable wall systems operable to partition a large room into a smaller room. More particularly, the present disclosure relates to a movable wall panel system having a plurality of electrical connections and a method for installing electrical appliances thereon.

Operable walls or partitions, also known as movable wall panel systems, find useful applications in a variety of venues such as classrooms, offices, convention facilities, hospitals or the like. In these venues, the operable partitions are often moved along overhead tracks from which the partitions are suspended. The partitions are movable along the tracks to separate or compartmentalize larger rooms into smaller rooms or areas. The operable partitions are typically connected to trolleys that roll within the overhead track. The track is suspended from a support structure which is typically located above the ceiling of a room in which the operable partitions are installed.

Operable partitions are typically available in single panel, paired panel, and continuously hinged arrangements. Paired panel systems are hinged together in groups of two panels which are either top supported by an overhead track or floor supported. Continuously hinged panels are connected together in a train so that the panels extend as one complete unit.

The movable wall panel system of the present disclosure includes a self-contained electrical system that moves with the wall panels during installation. Modular components of the electrical system facilitate repair or replacement of damaged components. The electrical system permits power receptacles to be located on the movable panels at desired locations. Electrical connection between adjacent panels is automatically provided as the panels are unfolded and then connected to an adjacent panel. In addition to providing electrical power to the panels, an electrical signal is used to validate proper electrical connection between the wall panels. Illustratively, a controller sends a test signal through the panels. The controller uses the test signal to determine whether or not the wall panels are properly connected. If the panels are not properly connected, the controller generates an alert signal for an operator.

In an illustrated embodiment of the present disclosure, a movable wall panel system includes a plurality of movable wall panels. Each of the plurality of panels includes first and second spaced apart ends and opposing sides. The panels are movable between a folded storage position and an extended use position in which the panels are substantially coplanar. Each of the plurality of panels has a first electrical connector located adjacent the first end and a second electrical connector located adjacent the second end. The first and second electrical connectors of each panel are electrically coupled together by an electrical wire extending through the panel to conduct electricity between the first and second electrical connectors of each panel. The first electrical connector of one panel is automatically coupled to the second electrical connector of an adjacent panel as the panels are moved from the folded storage position to the extended use position to electrically couple the adjacent panels together automatically. At least one of the plurality of panels has an electrical receptacle coupled to its associated first and second electrical connectors to provide an electrical power outlet on the at least one panel.

In one exemplary embodiment, the plurality of movable wall panels include a plurality of a hinged portions. The hinge portions are movable to move the adjacent panels between the folded storage portion and the extended use position. The first and second electrical connectors are located adjacent the hinged portion so that an electrical connection is automatically made between the first and second electrical connectors of the adjacent panels as the hinged portion is moved to move the first and second panels to the extended use position.

Additional features of the present system will become apparent to those skilled in the art upon consideration of the following detailed description of illustrative embodiments exemplifying the best mode of carrying out the present system and method as presently perceived.

BRIEF DESCRIPTION OF THE DRAWINGS

The detailed description particularly refers to the accompanying figures in which.

DETAILED DESCRIPTION OF THE DRAWINGS

Figure 1:
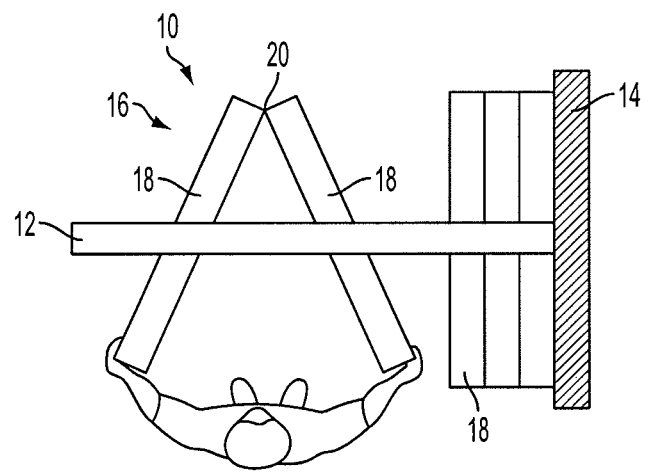
FIG. 1 is a diagrammatical view illustrating a paired panel operable partition.

For the purposes of promoting an understanding of the principles of the present disclosure, reference is now made to the embodiments illustrated in the drawings, which are described below. The embodiments disclosed below are not intended to be exhaustive or limit the present disclosure to the precise form disclosed in the following detailed description. Rather, the embodiments are chosen and described so that others skilled in the art may utilize their teachings. Therefore, no limitation of the scope of the present disclosure is thereby intended. The present system and method includes any alterations and further modifications of the illustrated devices and described methods and further applications of the principles of the present disclosure which would normally occur to one skilled in the art to which the present disclosure relates. Corresponding reference characters indicate corresponding parts throughout the several views.

The present disclosure relates to movable walls including self supported wall systems, operable partitions or demountable wall systems, for example, that may be erected in an environment such as in a room of a building. In one embodiment, an overhead truss (not shown) is used to support an overhead track 12 in the ceiling of the room. The track 12 supports movable wall panels 18, 24 of the wall system 10, 22 in a conventional manner. Floor supported panels may also be used.

Figure 2:
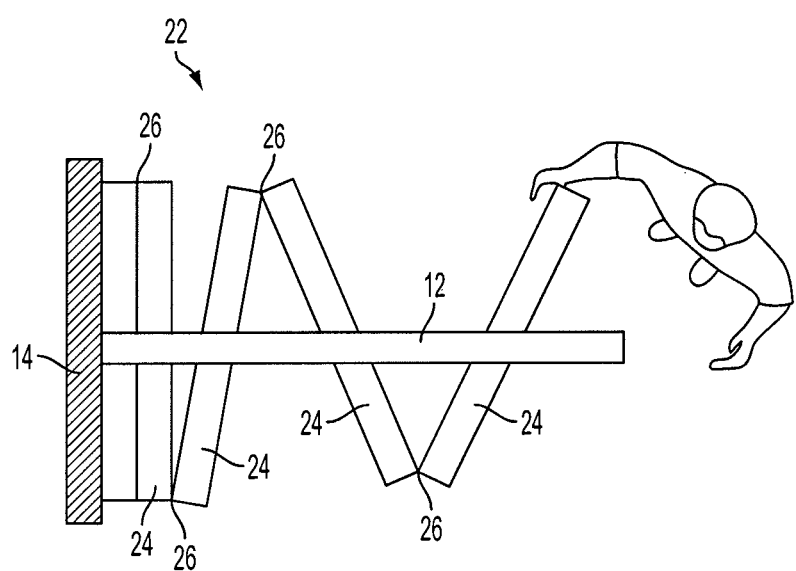
FIG. 2 is a diagrammatical view illustrating an operable partition having a plurality of continuously hinged panels connected together in a train and extending away from a wall.

In one illustrated embodiment, panels 18, 24 of a movable wall system 10, 22 are suspended from the track 12 such that they are movable between a folded (stored) position and an extended (use) position. Referring to FIG. 1, a first movable wall system 10 located adjacent a wall 14 is shown having paired panel segments 16 including two panels 18 connected by a hinge portion 20. Each two-panel segment 16 is unfolded and attached to an adjacent two-panel segment 16 to form a wall. Referring to FIG. 2, a second movable wall system 22 is shown having a plurality of panels 24 hinged together in a train by hinged portions 26 at opposite ends of the panels 22 to form a continuous wall. The panels 22 may be deployed manually as shown in FIG. 2 or automatically deployed using a drive motor and a control switch.

Figure 3:
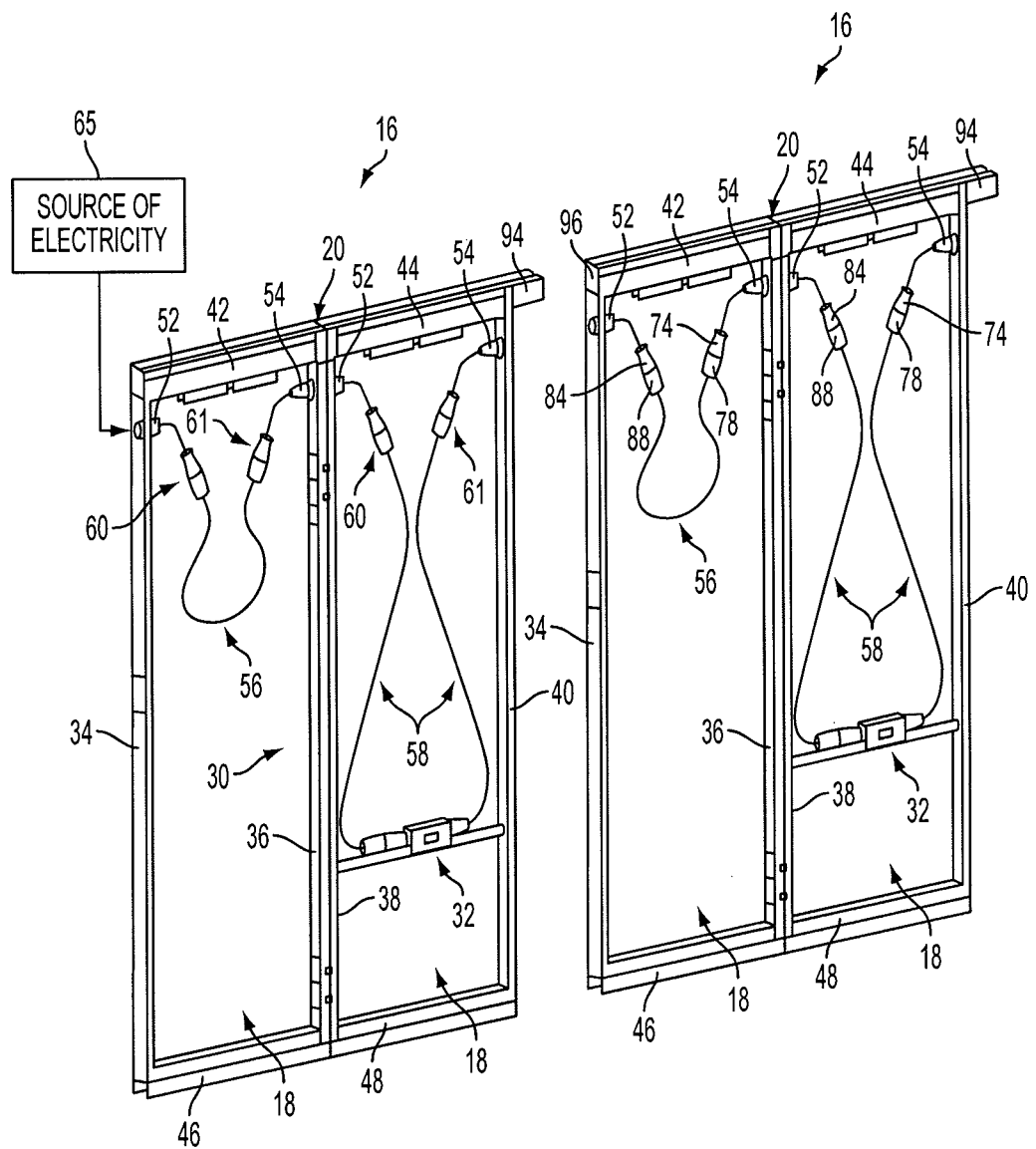
FIG. 3 is a perspective view illustrating first and second paired panels having a self-contained electrical system therein which automatically provides an electrical connection upon installation of the operable partition to provide electrical power to the wall panels.
Figure 6:
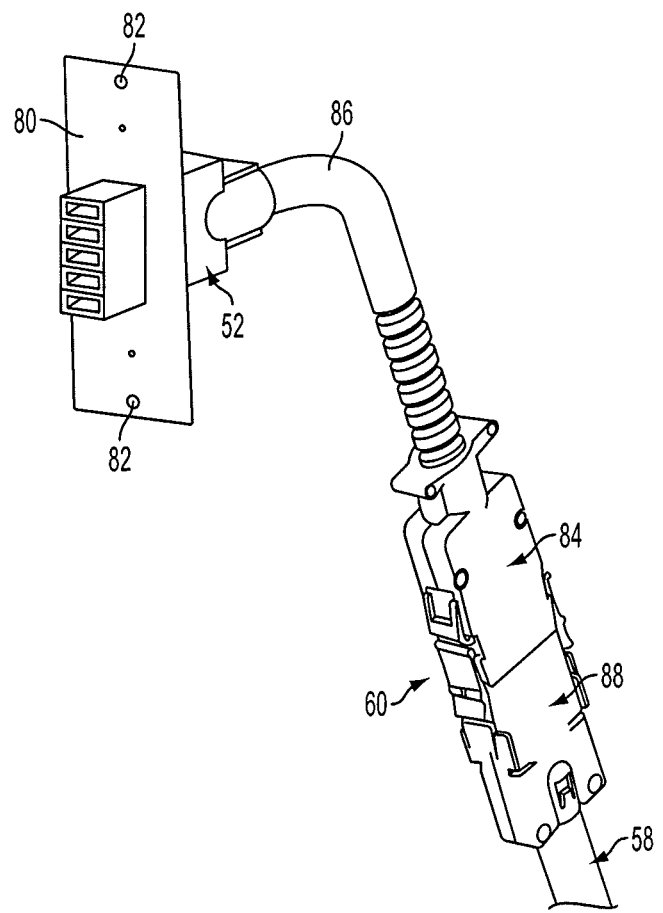
FIG. 6 is a perspective view of the female electrical connector of FIG. 4.
Figure 7:
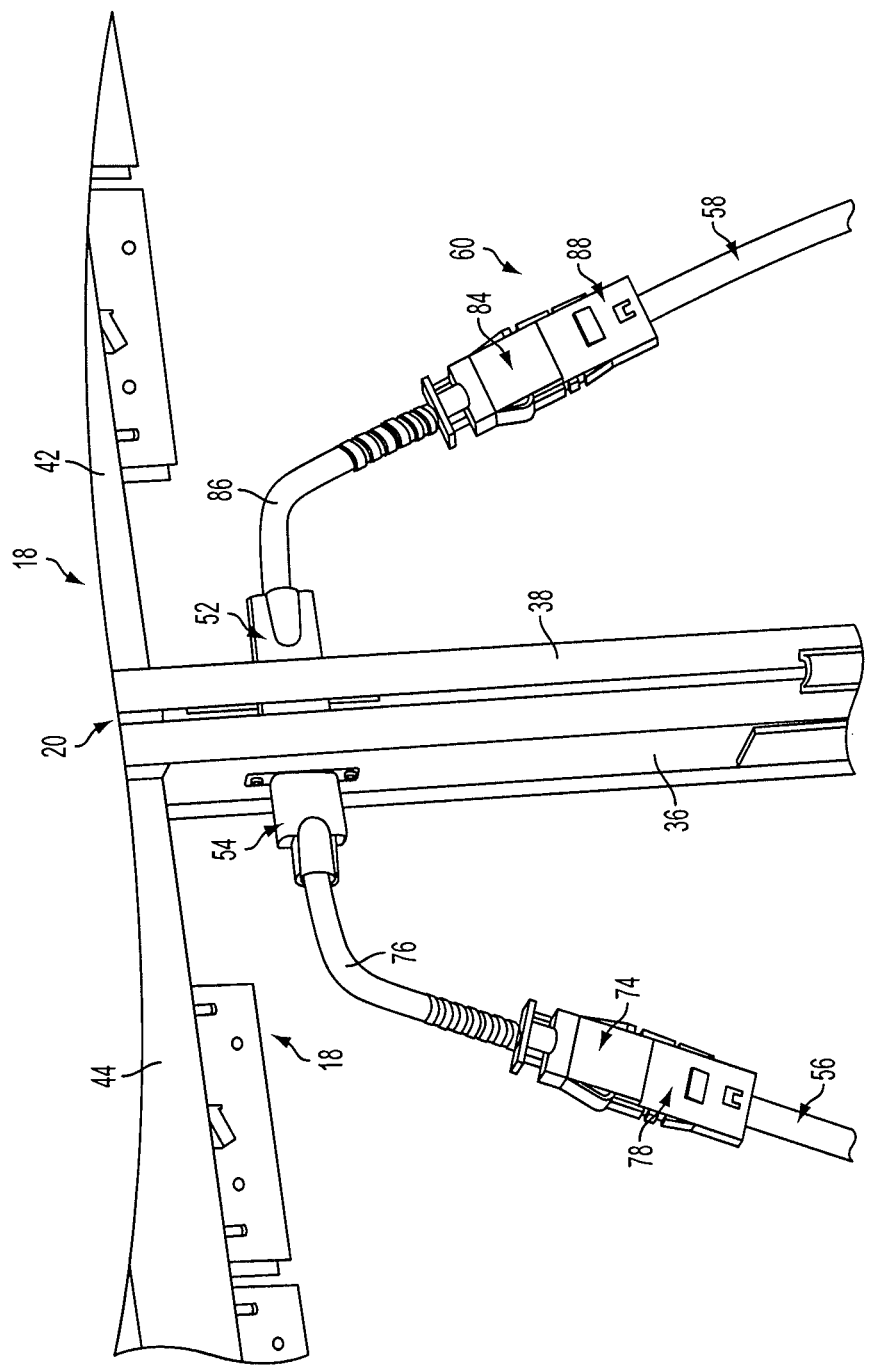
FIG. 7 is a perspective view illustrating the hinged panels of FIG. 4 in an open position in which electrical connection is made between the male and female connectors to provide electrical power to the panels.
Figure 8:
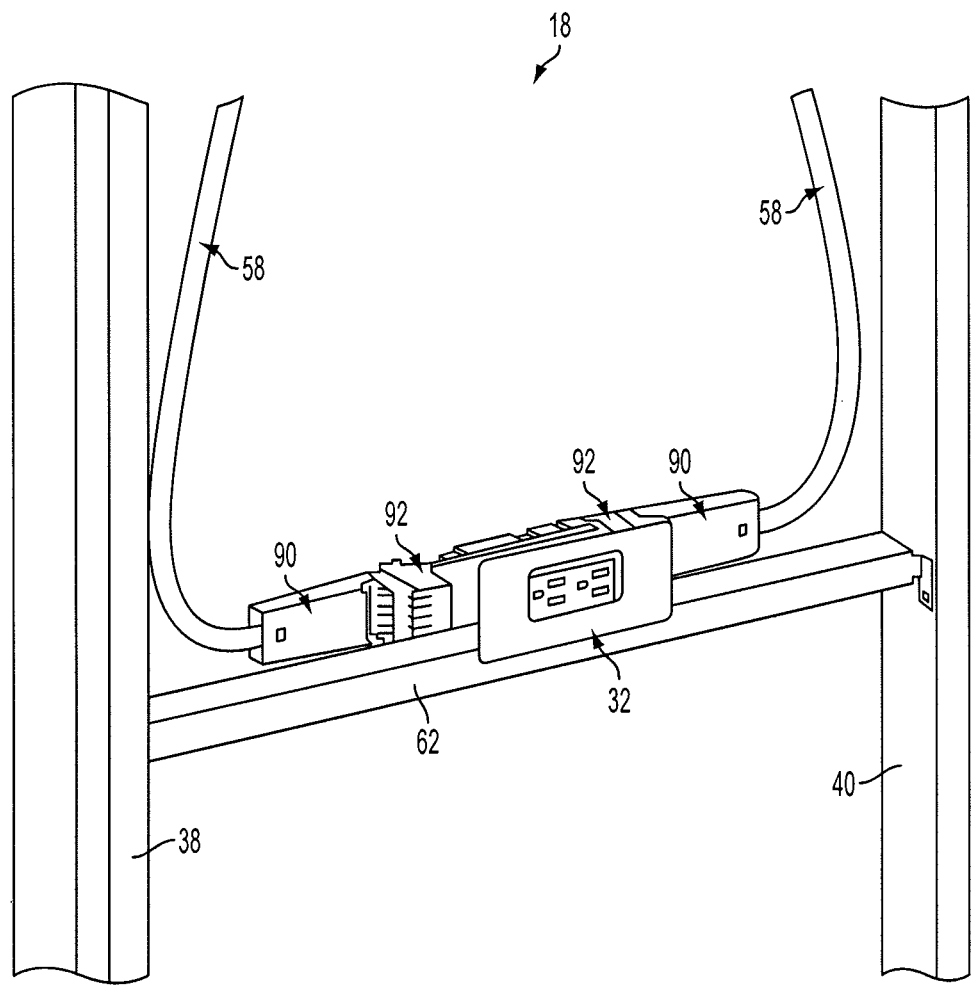
FIG. 8 is an enlarged view illustrating an electrical receptacle which provides an electrical power outlet on one of the panels of FIG. 3.

The operable partitions of the present disclosure include a self-contained electrical system 30 such as shown, for example, in FIGS. 3-8 for providing a plurality of electrical power receptacles 32 as best shown in FIGS. 3 and 8. FIG. 3 illustrates two paired panel segments 16 including hinged panels 18 foldable about a hinged portion 20. Panels 18 include vertical frame members 34, 36, 38 and 40 and horizontal frame members 42, 44, 46 and 48 which form the paired panel segment 16. An outer skin 50 covers the frame members of the panels 18 in a conventional manner to conceal components of the electrical system 30 as shown, for example, in FIGS. 10 and 11.

Each panel 18 includes first and second types of electrical connectors 52 and 54, respectively. Illustratively, electrical connectors 52 are female connectors and electrical connectors 54 are male connectors. Connectors 52 are configured to mate with connectors 54 as discussed below to provide an electrical connection between the panels 18. Continuous electrical connection through the panels 18 is provided by jumpers 56 and 58. Jumper 56 provides a connection between electrical connectors 52 and 54 of panel 18 via connector assemblies 60 and 61.

Jumpers 58 are connected to the electrical receptacle 32 which provides a power outlet on one panel 18. Receptacle 32 is coupled to a horizontal support rail 62 extending between vertical frame members 38 and 40 of panel 18. The location of horizontal support 32 may be selected to position the receptacle 32 at any desired height on the panels 18. While the receptacle 32 is shown on the right panel 18, the left panel 18 may also include a receptacle, if desired. Other panel segment 16 may include two jumpers 56 without any receptacles 32, if desired.

Figure 4:
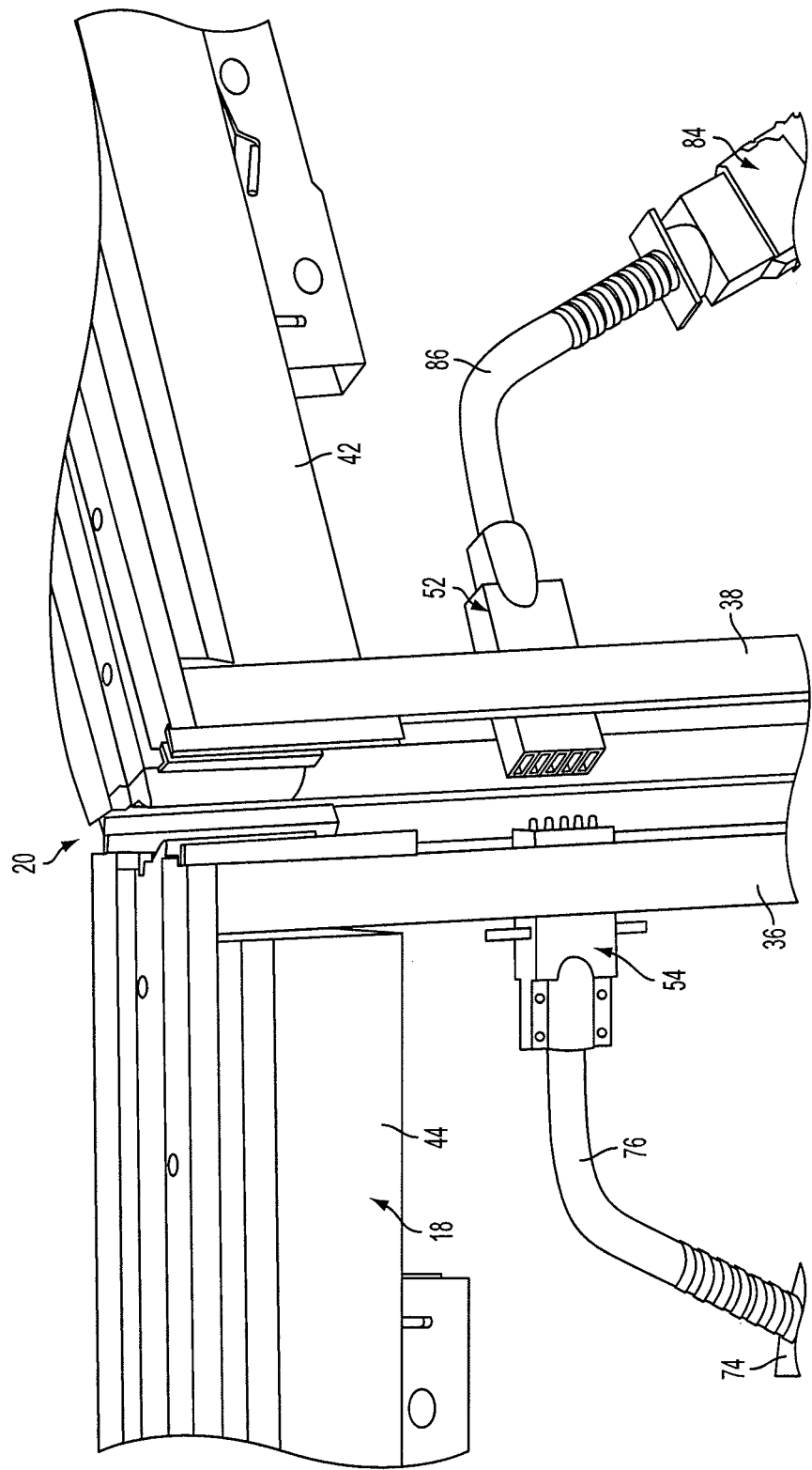
FIG. 4 is an enlarged perspective view illustrating male and female electrical connectors on opposite sides of a hinged portion of one of the paired panels of FIG. 3.

Electrical connectors 52 and 54 are positioned on the vertical frame members 36 and 38 of hinged portion 20, respectively, so that an electrical connection is automatically made between adjacent panels 18 as the hinged portion 20 is unfolded. Additional details of the hinged portion 20 are shown in FIGS. 4 and 7. In FIG. 4, the panels 18 are partially unfolded to show the connectors 52, 54. As the unfolding of panels 18 continues to align the adjacent panels 10 in a generally coplanar use position, the connectors 52 and 54 automatically mate or engage to provide the electrical connection between adjacent panels 18. FIG. 4 shows the connectors 52 and 54 still spaced apart. When the panels 18 are fully extended to the generally coplanar position shown in FIG. 7, the connectors 52 and 54 are fully engaged to provide the electrical connection.

Figure 5:
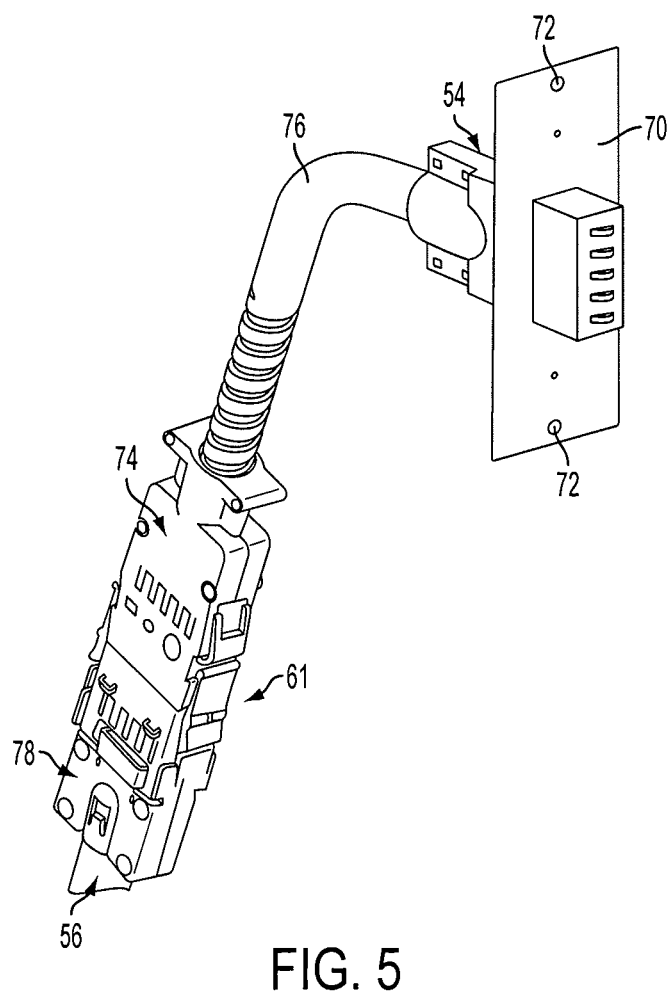
FIG. 5 is a perspective view of the male electrical connector of FIG. 4.

Additional details of the male electrical connector 54 are shown in FIG. 5. In an illustrated embodiment, a face plate 70 is coupled to the electrical connector 54. The face plate 70 is connected to one of vertical frame members 36, 40 of panels 18 by suitable fasteners (not shown) which extend through apertures 72 in face plate 70. Male connector 54 is illustratively coupled to a first connecting portion 74 of connector assembly 61 by a flexible, shielded conduit 76. Conduit 76 illustratively contains at least one electrical wire therein to provide electricity from male connector 54 to connector 74. Of course, the electrical wires may be used without the shielded conduit 76. Connector 74 is configured to mate with another connector 78 of jumper 56 or jumper 58. Other electrical wires within conduit 76 may provide electrical signals to test the whether the electrical system 30 is properly connected. Optional data signal lines may also be provided within the conduit 76.

Additional details of the female electrical connector 52 are shown in FIG. 6. A face plate 80 is coupled to the electrical connector 52. The face plate 80 is connected to one of vertical frame members 34, 38 of panels 18 by suitable fasteners (not shown) which extend through apertures 82 in face plate 80. Female connector 52 is coupled to a first connecting portion 84 of connector assembly 60 by a flexible, shielded conduit 86. Conduit 86 illustratively contains at least one electrical wire therein to provide electricity from female connector 52 to connector 84. Connector 84 is configured to mate with another connector 88 of jumper 58 or jumper 56. Other electrical wires within conduit 86 may provide electrical signals to test the whether the electrical system 30 is properly connected. Optionally, data signal lines may also be provided within the conduit 86. Again, the electrical wires and/or lines may be used without the shielded conduit 86.

FIG. 8 shows additional details of the electrical outlet receptacle 32 coupled to support rail 62. In the illustrated embodiment, connectors 90 of jumpers 58 are coupled to mating connectors 92 of receptacle 32 to provide electrical power to the receptacle 32. As discussed above, the support 62 may be positioned at any desired location during manufacture or installation of the panels 18 to position the power receptacle 32 at a desired location.

A source of electricity 65 is connected to an electrical connector 52 or 54 at one end of the operable partition. The source of electricity 65 is preferably located within the wall 14 of the building. In one embodiment, a switch is provided to selectively turn the supply of electricity on and off.

As shown in FIG. 3, the source of electricity 65 is connected to connector 52 or 54 at one end of the operable partition. As illustrated in FIG. 3, electricity flows from the source of electricity 65 through connector 52 and jumper 56 to connector 54 adjacent vertical frame member 36. Connector 54 of adjacent frame member 36 is automatically connected to connector 52 coupled to vertical frame member 38 when the panels 18 are in the unfolded, use position shown in FIG. 3. Electricity flows through connector 52 and first jumper 58 to the electrical receptacle 32. Electricity flows from the electrical receptacle 32 through second jumper 58 to electrical connector 54 coupled to vertical support 40.

When adjacent paired segments 16 of the operable partition are coupled together, the electrical connector 54 adjacent vertical support 40 is coupled to an electrical connector 52 adjacent vertical support 34 of the next panel segment 16 as illustrated in FIG. 3. In the illustrated embodiment, the panels 18 include a projection 94 adjacent a top one end of horizontal frame member 44 and a slot 96 adjacent the opposite end of frame member 42. Insertion of the projection 94 into the slot 96 provides initial alignment between adjacent panel segments 16 to facilitate the connection between connectors 54 and 52 as the panel segments 16 are joined.

Figure 11:
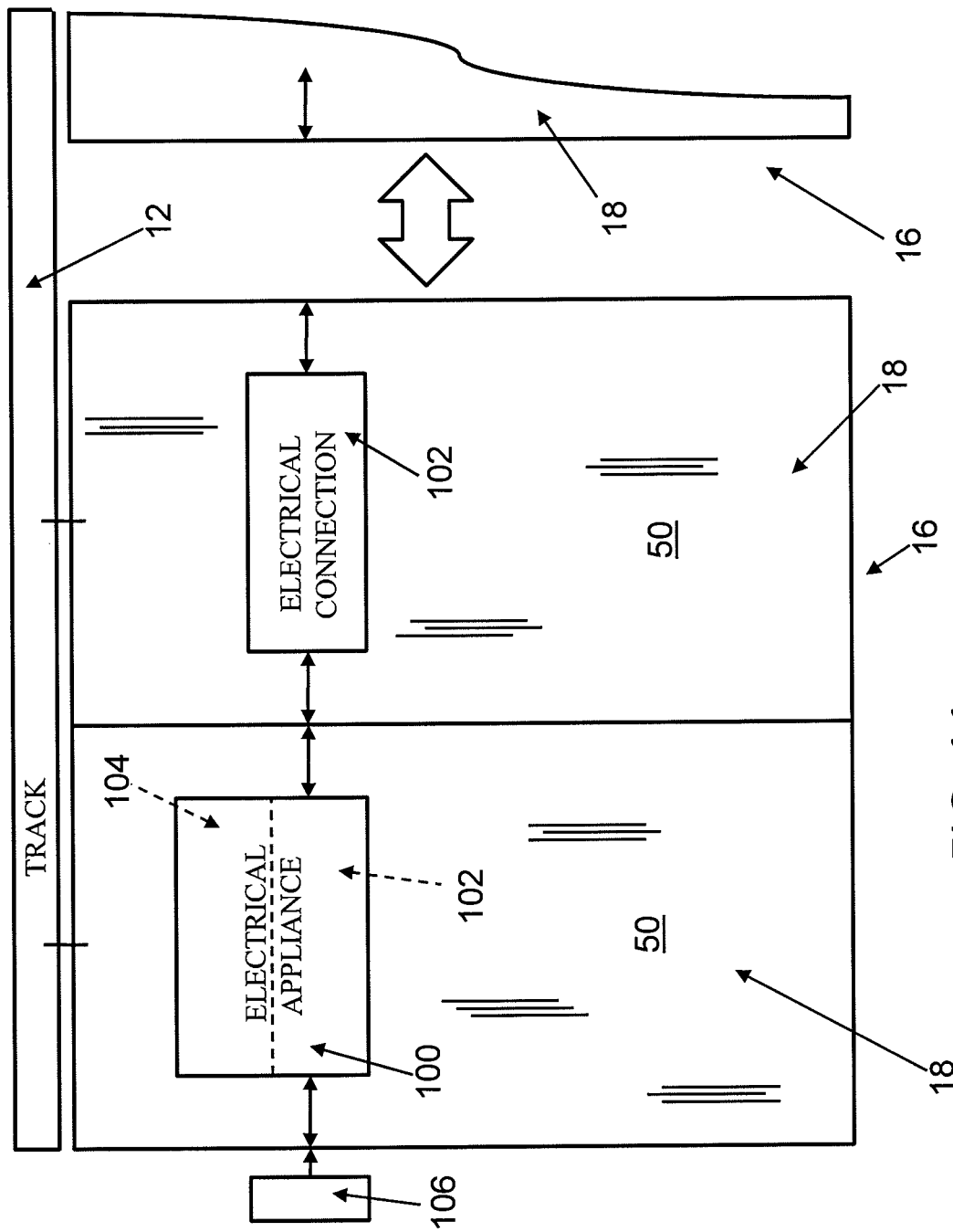
FIG. 11 illustrates connection of the paired panels to an adjacent paired panel segment and connection of one of the electrical appliances to the electrical and mechanical connections on one of the panels.

Once all the panels 18 are deployed to divide the room into a desired configuration and all the electrical connections are made between the electrical connectors 52 and 54 and adjacent panels 18, the electrical connection may be tested by sending a signal through the panels from a controller 106 shown in FIG. 11. If the controller 106 detects that a proper electrical connection has been established between all the panels 18, an indicator is provided. In addition, if the controller 106 determines an electrical connection has not been made between the panels 18, an alert signal is provided to the operator so that the operator may perform the necessary troubleshooting. The power cable or a separate signal line may be used for the test signal.

The modular design of the electrical system 30 including the electrical connectors 52, 54 and jumpers 56, 58 described above facilitates repair and replacement of components which may be damaged during repeated installation and breakdown of the operable partitions. The operator may disconnect the defective electrical component from mating connectors and replace components of the electrical system 30 without having to replace the entire system 30.

Figure 9:
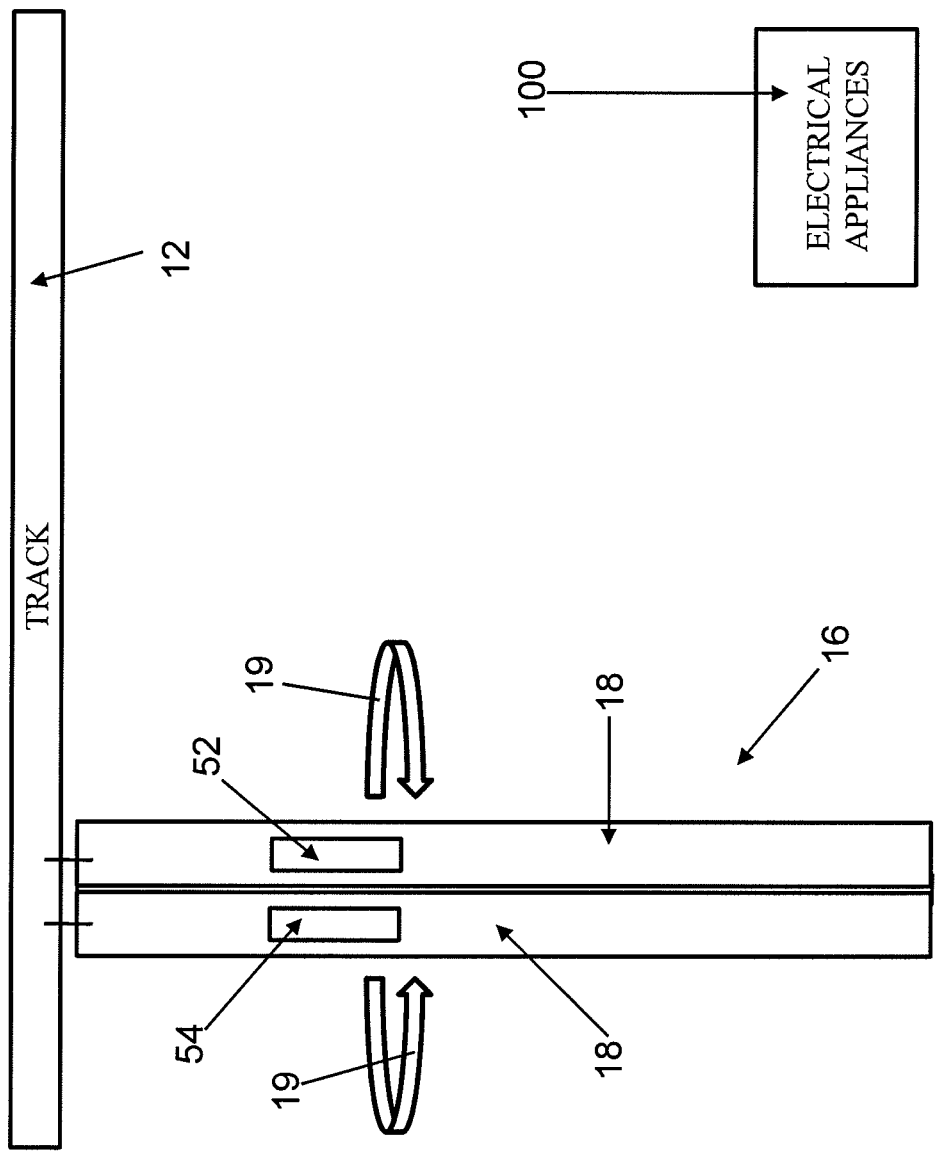
FIG. 9 is a diagrammatical view illustrating one of the paired panels in a folded storage position and illustrating a plurality of electrical appliances configured to be coupled to the wall panels.
Figure 10:
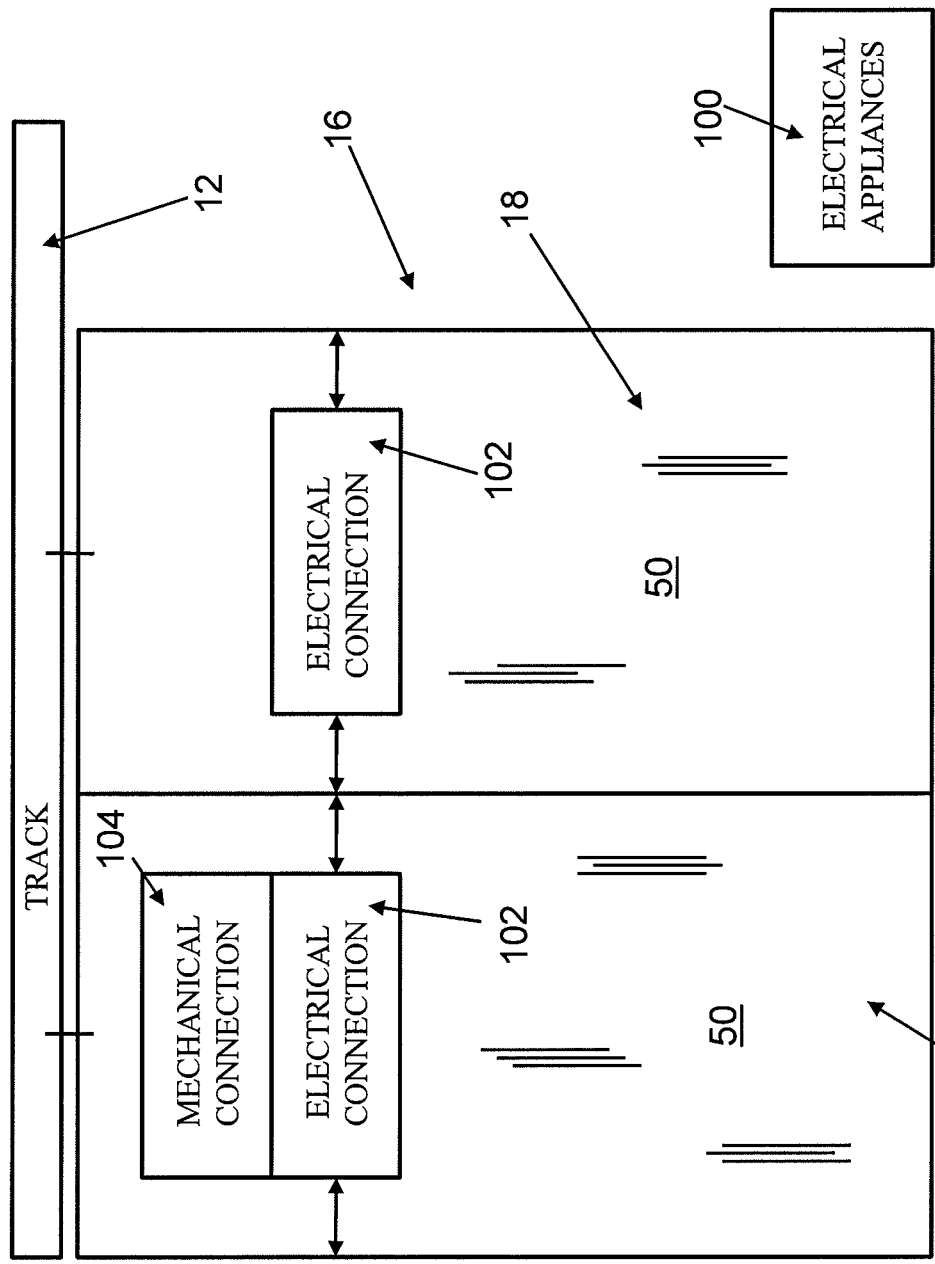
FIG. 10 illustrates the paired panel of FIG. 9 in an unfolded, deployed position in which an electrical connection is established by male and female electrical connector located at a hinged portion of the paired panels and illustrating mechanical and electrical connections for the electrical appliances on one of the panels.

FIGS. 9-11 illustrate an embodiment of the present disclosure in which a plurality of electrical appliances 100 such as, for example, lights are connected to the panels 18 of the operable partition. In an illustrated embodiment, the panels 18 of paired panel segment 16 are pivoted about the connection of hinged portion 20 in the directions of arrows 19 shown in FIG. 9 to move the panels 18 from the folded position to the extended use position shown in FIG. 10. A plurality of electrical appliances 100 are stored when the panels 18 of the operable partition are in the stored position of FIG. 9. As discussed in detail above, pivoting the panels 18 in the directions of arrows 19 in FIG. 9 causes electrical connectors 52 and 54 to automatically mate with each other and provide an electrical connection through the panels 18. The electrical connection 102 shown diagrammatically in FIG. 10 illustratively includes the jumpers 56 and 58 and electrical receptacle 32 described above or other type of electrical connection. In addition, at least one of the panels 18 includes a mechanical connection 104 located adjacent one of the electrical connections 102. The mechanical connection 104 may be a mounting bracket or other support located within the panel adjacent the electrical connection 102.

After the panels 18 are moved to the extended use position shown in FIG. 10, the paired panel segment 16 is then coupled to an adjacent paired panel section 16 as discussed above and shown, for example, in FIGS. 3 and 11. FIG. 11 also illustrates an electrical appliance coupled to the mechanical connection 104 and electrical connection 102 of panel 18. Therefore, the present disclosure provides a method for facilitating installation of electrical appliances within a portion of a room divided into a smaller room by panels 18. Providing integrated electrical and mechanical connectors 102 and 104 facilitates installation of the electrical appliances 100 at desired locations to provide lighting or other desired electrical appliances 100 at desired locations within the modified room.

The electrical system 30 may be used with many different varieties of operable partitions in track systems. For example, single panel systems, paired panel systems or continuously hinged panel systems may be used. For the continuously hinged panel system 22 shown in FIG. 2, connectors 52, 54 are provided in the hinged portions 26 between each adjacent panel 24. The panels may have various interface options and drop seal options. For example, Acousti-Seal® Operable Partitions, Multi-Directional Aluminum Suspension Systems RT100/RT200, and Smart Track™ Programmable Steel Suspension Systems available from Modernfold, Inc., all of which are incorporated herein by reference, may be used.

While this disclosure has been described as having exemplary designs and embodiments, the present systems and methods may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A method of dividing a space with a plurality of movable wall panels suspended from an overhead track, at least two of the moveable wall panels being operatively coupled together through at least one hinge and are movable about the at least one hinge between a folded storage position and an extended use position in which the panels are substantially coplanar, the method comprising the steps of:
   moving the at least two moveable wall panels along the track from the folded storage position to the extended use position; and
   automatically coupling a first electrical connector of a first moveable wall panel of the at least two moveable wall panels to a second electrical connector of a second moveable wall panel of the at least two moveable wall panels during the step of moving the at least two moveable wall panels along the track from the folded storage position to the extended use position, the first electrical connector of the first moveable wall panel of the at least two moveable wall panels being spaced apart from the second electrical connector of the second moveable wall panel of the at least two moveable wall panels when the at least two moveable wall panels are in the folded storage position and the first electrical connector of the first moveable wall panel of the at least two moveable wall panels contacting the second electrical connector of the second moveable wall panel of the at least two moveable wall panels when the at least two moveable wall panels are in the extended use position.

2. The method of claim 1, further comprising the step of: automatically coupling a third electrical connector of a third moveable wall panel of the at least two moveable wall panels to a fourth electrical connector of a fourth moveable wall panel of the at least two moveable wall panels during the step of moving the at least two moveable wall panels along the track from the folded storage position to the extended use position, the third electrical connector of the third moveable wall panel of the at least two moveable wall panels being spaced apart from the fourth electrical connector of the fourth moveable wall panel of the at least two moveable wall panels when the at least two moveable wall panels are in the folded storage position and the third electrical connector of the third moveable wall panel of the at least two moveable wall panels contacting the fourth electrical connector of the fourth moveable wall panel of the at least two moveable wall panels when the at least two moveable wall panels are in the extended use position.

3. The method of claim 2, further comprising the step of: electrically coupling a fifth electrical connector of the second moveable wall panel of the at least two moveable wall panels to a sixth electrical connector of the third moveable wall panel of the least two moveable wall panels.

4. The method of claim 3, wherein the step of moving the at least two moveable wall panels along the track from the folded storage position to the extended use position includes the steps of:
rotating the first moveable wall panel relative to the second moveable wall panel about a first hinge of the at least one hinge, the first hinge coupling the first moveable wall panel to the second moveable wall panel when the first moveable wall panel and the second moveable wall panel are in the folded stored position;
rotating the third moveable wall panel relative to the fourth moveable wall panel about a second hinge of the at least one hinge, the second hinge coupling the third moveable wall panel to the fourth moveable wall panel when the third moveable wall panel and the fourth moveable wall panel are in the folded stored position; and
rotating the second moveable wall panel relative to the third moveable wall panel about a third hinge of the at least one hinge, the third hinge coupling the third moveable wall panel to the second moveable wall panel when the third moveable wall panel and the second moveable wall panel are in the folded stored position.

5. The method of claim 3, wherein the step of moving the at least two moveable wall panels along the track from the folded storage position to the extended use position includes the steps of:
rotating the first moveable wall panel relative to the second moveable wall panel about a first hinge of the at least one hinge, the first hinge coupling the first moveable wall panel to the second moveable wall panel when the first moveable wall panel and the second moveable wall panel are in the folded stored position;
rotating the third moveable wall panel relative to the fourth moveable wall panel about a second hinge of the at least one hinge, the second hinge coupling the third moveable wall panel to the fourth moveable wall panel when the third moveable wall panel and the fourth moveable wall panel are in the folded stored position;
translating the second moveable wall panel relative to the third moveable wall panel to bring the second movable wall panel into contact with the third moveable wall panel; and
receiving a projection of the second moveable wall panel within a slot of the third moveable wall panel as the second moveable wall panel is translated relative to the third moveable wall panel.

6. The method of claim 5, wherein the step of receiving the projection of the second moveable wall panel within the slot of the third moveable wall panel as the second moveable wall panel is translated relative to the third moveable wall panel results in the fifth electrical connector of the second moveable wall panel being aligned with the sixth electrical connector of the third moveable wall panel.

7. The method of claim 3, further comprising the steps of:
determining whether the first moveable wall panel is electrically coupled to the fourth moveable wall panel when the first moveable wall panel, the second moveable wall panel, the third moveable wall panel, and the fourth moveable wall panel are in the extended use position; and
providing an alert signal in response to a determination that the first moveable wall panel is not electrically coupled to the fourth moveable wall panel.

* * * * *

UNITED STATES PATENT AND TRADEMARK OFFICE
CERTIFICATE OF CORRECTION

PATENT NO. : 9,682,134 B2
APPLICATION NO. : 15/248893
DATED : June 20, 2017
INVENTOR(S) : Bryan Thomas Welch et al.

It is certified that error appears in the above-identified patent and that said Letters Patent is hereby corrected as shown below:

In the Claims

In Claim 3, Column 7, Line 31, insert the word --at-- before the word "least".

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*